(12) United States Patent
Callaghan et al.

(10) Patent No.: US 8,636,765 B2
(45) Date of Patent: *Jan. 28, 2014

(54) CATCH MEMBER FOR PFO OCCLUDER

(71) Applicant: W.L. Gore & Associates, Inc., Flagstaff, AZ (US)

(72) Inventors: David J. Callaghan, Boston, MA (US); Erik N. Glaser, Waltham, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/857,527

(22) Filed: Apr. 5, 2013

(65) Prior Publication Data

US 2013/0226228 A1    Aug. 29, 2013

Related U.S. Application Data

(63) Continuation of application No. 13/631,557, filed on Sep. 28, 2012, now Pat. No. 8,430,907, which is a continuation of application No. 11/384,635, filed on Mar. 20, 2006, now Pat. No. 8,277,480.

(60) Provisional application No. 60/663,289, filed on Mar. 18, 2005.

(51) Int. Cl.
*A61B 17/08* (2006.01)
*A61D 1/00* (2006.01)

(52) U.S. Cl.
USPC ................................................... 606/213

(58) Field of Classification Search
USPC ................. 606/151–158, 200, 213, 215; 623/23.72–23.76
See application file for complete search history.

(56) References Cited

U.S. PATENT DOCUMENTS

| | | |
|---|---|---|
| 3,824,631 A | 7/1974 | Burstein et al. |
| 3,874,388 A | 4/1975 | King et al. |
| 3,875,648 A | 4/1975 | Bone |
| 3,924,631 A | 12/1975 | Mancusi |
| 4,006,747 A | 2/1977 | Kronenthal et al. |
| 4,007,743 A | 2/1977 | Blake |
| 4,149,327 A | 4/1979 | Hammer et al. |
| 4,425,908 A | 1/1984 | Simon |
| 4,610,674 A | 9/1986 | Suzuki et al. |
| 4,626,245 A | 12/1986 | Weinstein |

(Continued)

FOREIGN PATENT DOCUMENTS

| | | |
|---|---|---|
| DE | 9413645 U1 | 10/1994 |
| EP | 0474887 A1 | 3/1992 |

(Continued)

OTHER PUBLICATIONS

ISR of PCT/US97/17927, (1 pg), Feb. 10, 1998.

(Continued)

*Primary Examiner* — Melanie Tyson
(74) *Attorney, Agent, or Firm* — DLA Piper LLP (US)

(57) ABSTRACT

Delivery (and recovery) devices and techniques for delivering an implant into a desired location within the body and catch systems for such implants. The devices and techniques relate particularly to, but are not limited to, a patent foramen ovale (PFO) occluder made from a polymer tube. A catch system maintains an occluder in a deployed configuration by holding it in a reduced axial length position. Some embodiments have a compressible tip. Some embodiments have temporary catching mechanisms.

10 Claims, 6 Drawing Sheets

(56) References Cited

U.S. PATENT DOCUMENTS

| | | |
|---|---|---|
| 4,696,300 A | 9/1987 | Anderson |
| 4,710,192 A | 12/1987 | Liotta et al. |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,078,736 A | 1/1992 | Behl |
| 5,106,913 A | 4/1992 | Yamaguchi et al. |
| 5,108,420 A | 4/1992 | Marks |
| 5,149,327 A | 9/1992 | Oshiyama et al. |
| 5,167,363 A | 12/1992 | Adkinson et al. |
| 5,167,637 A | 12/1992 | Okada et al. |
| 5,171,259 A | 12/1992 | Inoue et al. |
| 5,192,301 A | 3/1993 | Kamiya et al. |
| 5,222,974 A | 6/1993 | Kensey et al. |
| 5,226,879 A | 7/1993 | Ensminger et al. |
| 5,236,440 A | 8/1993 | Hlavacek |
| 5,245,023 A | 9/1993 | Peoples et al. |
| 5,245,080 A | 9/1993 | Aubard et al. |
| 5,250,430 A | 10/1993 | Peoples et al. |
| 5,257,637 A | 11/1993 | El Gazayerli |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,316,262 A | 5/1994 | Koebler |
| 5,334,217 A | 8/1994 | Das |
| 5,350,363 A | 9/1994 | Goode et al. |
| 5,354,308 A | 10/1994 | Simon et al. |
| 5,411,481 A | 5/1995 | Allen et al. |
| 5,413,584 A | 5/1995 | Schulze et al. |
| 5,417,699 A | 5/1995 | Klein et al. |
| 5,425,744 A | 6/1995 | Fagan et al. |
| 5,433,727 A | 7/1995 | Sideris |
| 5,451,235 A | 9/1995 | Lock et al. |
| 5,478,353 A | 12/1995 | Yoon |
| 5,480,353 A | 1/1996 | Garza, Jr. |
| 5,480,424 A | 1/1996 | Cox |
| 5,486,193 A | 1/1996 | Bourne et al. |
| 5,507,811 A | 4/1996 | Koike et al. |
| 5,534,432 A | 7/1996 | Peoples et al. |
| 5,540,712 A | 7/1996 | Kleshinski et al. |
| 5,562,632 A | 10/1996 | Davila et al. |
| 5,577,299 A | 11/1996 | Thompson et al. |
| 5,601,571 A | 2/1997 | Moss |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,649,959 A | 7/1997 | Hannam et al. |
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Schneidt et al. |
| 5,709,707 A | 1/1998 | Lock et al. |
| 5,717,259 A | 2/1998 | Schexnayder |
| 5,720,754 A | 2/1998 | Middleman et al. |
| 5,725,552 A | 3/1998 | Kotula et al. |
| 5,733,294 A | 3/1998 | Forber et al. |
| 5,733,337 A | 3/1998 | Carr, Jr. et al. |
| 5,741,297 A | 4/1998 | Simon |
| 5,776,162 A | 7/1998 | Kleshinski |
| 5,776,183 A | 7/1998 | Kanesaka et al. |
| 5,797,960 A | 8/1998 | Stevens et al. |
| 5,800,516 A | 9/1998 | Fine et al. |
| 5,810,884 A | 9/1998 | Kim |
| 5,823,956 A | 10/1998 | Roth et al. |
| 5,829,447 A | 11/1998 | Stevens et al. |
| 5,853,420 A | 12/1998 | Chevillon et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,879,366 A | 3/1999 | Shaw et al. |
| 5,893,856 A | 4/1999 | Jacob et al. |
| 5,902,319 A | 5/1999 | Daley |
| 5,904,703 A | 5/1999 | Gilson |
| 5,919,200 A | 7/1999 | Stambaugh et al. |
| 5,924,424 A | 7/1999 | Stevens et al. |
| 5,928,250 A | 7/1999 | Koike et al. |
| 5,944,738 A | 8/1999 | Amplatz et al. |
| 5,955,110 A | 9/1999 | Patel et al. |
| 5,976,174 A | 11/1999 | Ruiz |
| 5,989,268 A | 11/1999 | Pugsley, Jr. et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,024,756 A | 2/2000 | Huebsch et al. |
| 6,030,007 A | 2/2000 | Bassily et al. |
| 6,056,760 A | 5/2000 | Koike et al. |
| 6,071,998 A | 6/2000 | Muller et al. |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,165,183 A | 12/2000 | Kuehn et al. |
| 6,165,204 A | 12/2000 | Levinson et al. |
| 6,171,329 B1 | 1/2001 | Shaw et al. |
| 6,174,322 B1 | 1/2001 | Schneidt et al. |
| 6,174,330 B1 | 1/2001 | Stinson |
| 6,187,039 B1 | 2/2001 | Hiles et al. |
| 6,190,353 B1 | 2/2001 | Makower et al. |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,227,139 B1 | 5/2001 | Nguyen et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,446 B1 | 11/2001 | Huebsch et al. |
| 6,315,791 B1 | 11/2001 | Gingras et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |
| 6,346,074 B1 | 2/2002 | Roth |
| 6,348,041 B1 | 2/2002 | Klint et al. |
| 6,352,552 B1 | 3/2002 | Levinson et al. |
| 6,355,052 B1 | 3/2002 | Neuss et al. |

(56) References Cited

U.S. PATENT DOCUMENTS

| | | |
|---|---|---|
| 6,356,782 B1 | 3/2002 | Sirimanne et al. |
| 6,364,853 B1 | 4/2002 | French et al. |
| 6,371,904 B1 | 4/2002 | Sirimanne et al. |
| 6,375,625 B1 | 4/2002 | French et al. |
| 6,375,671 B1 | 4/2002 | Kobayashi et al. |
| 6,379,342 B1 | 4/2002 | Levinson |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,402,772 B1 | 6/2002 | Amplatz et al. |
| 6,419,669 B1 | 7/2002 | Frazier et al. |
| 6,426,145 B1 | 7/2002 | Moroni |
| 6,436,088 B2 | 8/2002 | Frazier et al. |
| 6,440,152 B1 | 8/2002 | Gainor et al. |
| 6,460,749 B1 | 10/2002 | Levinson et al. |
| 6,482,224 B1 | 11/2002 | Michler et al. |
| 6,488,706 B1 | 12/2002 | Solymar et al. |
| 6,494,888 B1 | 12/2002 | Laufer et al. |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,585,755 B2 | 7/2003 | Jackson et al. |
| 6,596,013 B2 | 7/2003 | Yang et al. |
| 6,599,448 B1 | 7/2003 | Ehrhard, Jr. et al. |
| 6,610,764 B1 | 8/2003 | Martin et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,666,861 B1 | 12/2003 | Grabek |
| 6,669,722 B2 | 12/2003 | Chen et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,828,357 B1 | 12/2004 | Martin et al. |
| 6,838,493 B2 | 1/2005 | Williams et al. |
| 6,867,247 B2 | 3/2005 | Williams et al. |
| 6,867,248 B1 | 3/2005 | Martin et al. |
| 6,867,249 B2 | 3/2005 | Lee et al. |
| 6,921,410 B2 | 7/2005 | Porter |
| 7,871,419 B2 | 1/2011 | Devellian et al. |
| 2001/0010481 A1 | 8/2001 | Blanc et al. |
| 2001/0014800 A1 | 8/2001 | Frazier et al. |
| 2001/0025132 A1 | 9/2001 | Alferness et al. |
| 2001/0034537 A1 | 10/2001 | Shaw et al. |
| 2001/0034567 A1 | 10/2001 | Allen et al. |
| 2001/0037129 A1 | 11/2001 | Thill |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Javaraman |
| 2002/0019648 A1 | 2/2002 | Akerfeldt et al. |
| 2002/0022860 A1 | 2/2002 | Borillo et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0049457 A1 | 4/2002 | Kaplan et al. |
| 2002/0052572 A1 | 5/2002 | Franco et al. |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0096183 A1 | 7/2002 | Stevens et al. |
| 2002/0099389 A1 | 7/2002 | Michler et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0164729 A1 | 11/2002 | Skraly et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0004533 A1 | 1/2003 | Dieck et al. |
| 2003/0023266 A1 | 1/2003 | Welch et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0059640 A1 | 3/2003 | Marton et al. |
| 2003/0065379 A1 | 4/2003 | Babbs et al. |
| 2003/0100920 A1 | 5/2003 | Akin et al. |
| 2003/0120337 A1 | 6/2003 | Van Tassel et al. |
| 2003/0139819 A1 | 7/2003 | Beer et al. |
| 2003/0171774 A1 | 9/2003 | Freudenthal et al. |
| 2003/0191495 A1 | 10/2003 | Ryan et al. |
| 2003/0195530 A1 | 10/2003 | Thill |
| 2003/0204203 A1 | 10/2003 | Khairkhahan et al. |
| 2004/0044361 A1 | 3/2004 | Frazier et al. |
| 2004/0073242 A1 | 4/2004 | Chanduszko |
| 2004/0176799 A1 | 9/2004 | Chanduszko et al. |
| 2004/0210301 A1 | 10/2004 | Obermiller |
| 2004/0234567 A1 | 11/2004 | Dawson |
| 2005/0025809 A1 | 2/2005 | Hasirci et al. |
| 2005/0043759 A1 | 2/2005 | Chanduszko |
| 2005/0113868 A1 | 5/2005 | Devellian |
| 2005/0267523 A1 | 12/2005 | Devellian et al. |
| 2005/0273135 A1 | 12/2005 | Chanduszko et al. |
| 2005/0288706 A1 | 12/2005 | Widomski et al. |
| 2005/0288786 A1 | 12/2005 | Chanduszko |
| 2006/0122647 A1 | 6/2006 | Callaghan et al. |
| 2006/0265004 A1 | 11/2006 | Callaghan et al. |
| 2007/0010851 A1 | 1/2007 | Chanduszko et al. |
| 2007/0167981 A1 | 7/2007 | Opolski |

FOREIGN PATENT DOCUMENTS

| | | |
|---|---|---|
| EP | 0 839 549 | 5/1998 |
| EP | 1013227 A2 | 6/2000 |
| EP | 1046375 A1 | 10/2000 |
| EP | 1222897 A2 | 7/2002 |
| WO | WO-96/25179 | 8/1996 |
| WO | WO-96/31157 | 10/1996 |
| WO | WO-98/07375 | 2/1998 |
| WO | WO-98/29026 | 7/1998 |
| WO | WO-98/51812 | 11/1998 |
| WO | WO-99/05977 | 2/1999 |
| WO | WO-99/18862 | 4/1999 |
| WO | WO-99/18864 | 4/1999 |
| WO | WO-99/18870 | 4/1999 |
| WO | WO-99/18871 | 4/1999 |
| WO | WO-00/27292 | 5/2000 |
| WO | WO-00/44428 | 8/2000 |
| WO | WO-01/21247 | 3/2001 |
| WO | WO-01/30268 | 5/2001 |
| WO | WO-01/49185 | 7/2001 |
| WO | WO-01/78596 | 10/2001 |
| WO | WO-02/17809 | 3/2002 |
| WO | WO-02/24106 | 3/2002 |
| WO | WO-03/024337 | 3/2003 |
| WO | WO-03/053493 | 7/2003 |
| WO | WO-03/059152 | 7/2003 |
| WO | WO-03/077733 | 9/2003 |
| WO | WO-03/082076 | 10/2003 |
| WO | WO-03/103476 | 12/2003 |
| WO | WO-2004/043266 | 5/2004 |
| WO | WO-2004/043508 | 5/2004 |
| WO | WO-2005/009220 | 10/2005 |

(56) References Cited

FOREIGN PATENT DOCUMENTS

| | | |
|---|---|---|
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

ISR of PCT/US02/40850 (4 pgs), Jun. 19, 2003.
ISR of PCT/US03/01050, (1 pg), Jul. 8, 2003.
ISR of PCT/US03/09051, (2pgs), Sep. 29, 2003.
ISR of PCT/US03/17390, (4 pgs), Oct. 6, 2003.
ISR of PCT/US03/34003, (4 pgs), Mar. 10, 2004.
ISR of PCT/US03/17715, (2 pgs), Mar. 24, 2004.
ISR of PCT/US03/35479, (2 pgs), Apr. 14, 2004.
ISR of PCT/US03/39253, (4 pgs), Apr. 19, 2004.
ISR of PCT/US03/32133, (1 pg), Apr. 22, 2004.
ISR of PCT/US03/35998, (5 pgs), Jun. 16, 2004.
ISR of PCT/US04/029978, (3 pgs), Jan. 26, 2005.
ISR of PCT/US04/022643, 2005 (2 pgs), Mar. 31, 2005.
ISR of PCT/US04/026998, (5 pgs), Apr. 22, 2005.
ISR of PCT/USOS/006703, (3 pgs), Jul. 25, 2005.
ISR of PCT/USOS/013705, (4 pgs), Aug. 4, 2005.
ISR of PCT/USOS/015382, (4 pgs), Oct. 5, 2005.
ISR of PCT/US06/09978, (2 pgs), Jul. 13, 2006.
ISR of PCT/EP06/010783, (6 pgs), May 4, 2007.
ISR of PCT/US2007/065541, (4 pgs), Aug. 7, 2007.
ISR of PCT/US2007/065526, (5 pgs), Aug. 8, 2007.
Eurpoean Examination Report, European Application No. 04781644.2, mailed Aug. 23, 2007, (3 Pages).
ISR of PCT/US07/065532, (5 pgs), Sep. 14, 2007.
ISR of PCT/US07/065532 (5 pgs), Sep. 14, 2007.
ISR of PCT/US07/065546 (4 pgs), Oct. 29, 2007.
Athanasion, T., "Coronary Artery Bypass with the Use of a Magnetic Distal Anastomotic Device: Surgical Technique and Preliminary Experience," The Heart Surgery Forum #2004-1024, 2004, 4 pgs.
Bachthaler, M. et al., "Corrosion of Tungsten Coils After Peripheral Vascular Embolization Theraphy: Influence on Outcome and Thingsten Load", *Catherization and Cardiovascular Interventions*, vol. 62, pp. 380-384, 2004.
Filsoufi, F., et al., "Automated Distal Coronary Bypass with a Novel Magnetic Coupler (MVP system)," J. Thoracic and Cardiovascular Surgery, vol. 127(1), pp. 185-192, 2004, The American Association for Thoracic Surgery.
Isotalo, T. et al., "Biocompatibility Testing of a New Bioabsorbable X-Ray Positive SR-PLA 96/4 Urethral Stent", The Journal of Urology, vol. 163, pp. 1764-1767, Nov. 1999.
Kimura, A., et al., "Effects of Neutron Irradiation on the Transformation Behavior in Ti-Ni Alloys," Abstract, Proceedings of the Int'l Conf. on Mariensitic Transformations, 1992, pp. 935-940.
Klima, U., "Magnetic Vascular Port in Minimally Invasive Direct Coronary Artery Bypass Grafting," Circulation 2004 II-55-II-60.
Meier, MD, Bernhard, et al., "Contemporary Management of Patent Foramen Ovale," American Heart Association, Inc., Circulation, 2003, vol. 107, pp. 5-9.
Parviainen, M. et al., "A New Biodegradable Stent for the Pancreaticojejunal Anastomosis After Pancreaticoduodenal Resection: In Vitro Examination and Pilot Experiences in Humans", *Pancreas*, vol. 21, No. 1, pp. 14-21, 2000.
Ramanathan, G., et al., "Experimental and Computational Methods for Shape Memory Alloys," 15th ASCE Engineering Mechanics Conference, Jun. 2-5, 2002.
Ruddy, A.C. et al., "Rheological, Mechanical and Thermal Behaviour of Radiopaque Filled Polymers", ANTEC Conference Proceedinas, vol. 8, pp. 167-171, 2005.
Ruiz, et al., "The Puncture Technique: A New Method for Transcatheter Closure of Patent Foramen Ovale," Catheterization and Cardiovascular Interventions, 2001, vol. 53, pp. 369-372.
Shabalovskaya, S., "Surface, Corrosion amd Biocompatibility Aspects of Nitinol as and Implant Material," Bio-Medical Materials and Engineering, 2002, vol. 12, pp. 69-109.
SMST-2000, "Proceedings of the International Conference on Shape Memory and Superelastic Technologies," Apr. 30 to May 4, 2000, Asilomar Conference Center.
Stockel, "Nitinol Medical Devices and Implants," SMST-2000 Conference Proceedings, 2001, pp. 531-541.
Uchil, J., "Shape Memory Alloys- Characterization Techniques," Pramana—Journal of Physics, 2002, vol. 58(5)(6), pp. 1131-1139.
Vaajanen, A. et al., "Expansion and Fixation Properties of a New Braided Biodegradable Urethral Stent: an Experimental Study in the Rabbit", The Journal of Urology, vol. 169, pp. 1771-1174, Mar. 2003.
Falk, V., "Facilitated Endoscopic Beating Heart Coronary Artery Bypass Grafting Using a Magnetic Coupling Device," Journal of Thoracic and Cardiovascular Surgery, vol. 126,(5), pp. 1575-1579, 2003.

CATCH MEMBER FOR PFO OCCLUDER

CROSS-REFERENCE TO RELATED APPLICATIONS

This application is a continuation application of U.S. application Ser. No. 13/631,557 filed Sep. 28, 2012, now issued as U.S. Pat. No. 8,430,907; which is a continuation application of U.S. application Ser. No. 11/384,635 filed Mar. 20, 2006, now issued as U.S. Pat. No. 8,277,480; which claims the benefit under 35 USC §119(e) to U.S. Application Ser. No. 60/663,289 filed Mar. 18, 2005, now expired. The disclosure of each of the prior applications is considered part of and is incorporated by reference in the disclosure of this application.

BACKGROUND OF THE INVENTION

1. Field of the Invention

This disclosure relates generally to an occlusion device for the closure of physical anomalies, such as an atrial septal defect, a patent foramen ovale (PFO), and other septal and vascular defects; the disclosure relates particularly catch systems and catch members for such a device.

2. Background of the Invention

Figure 1:
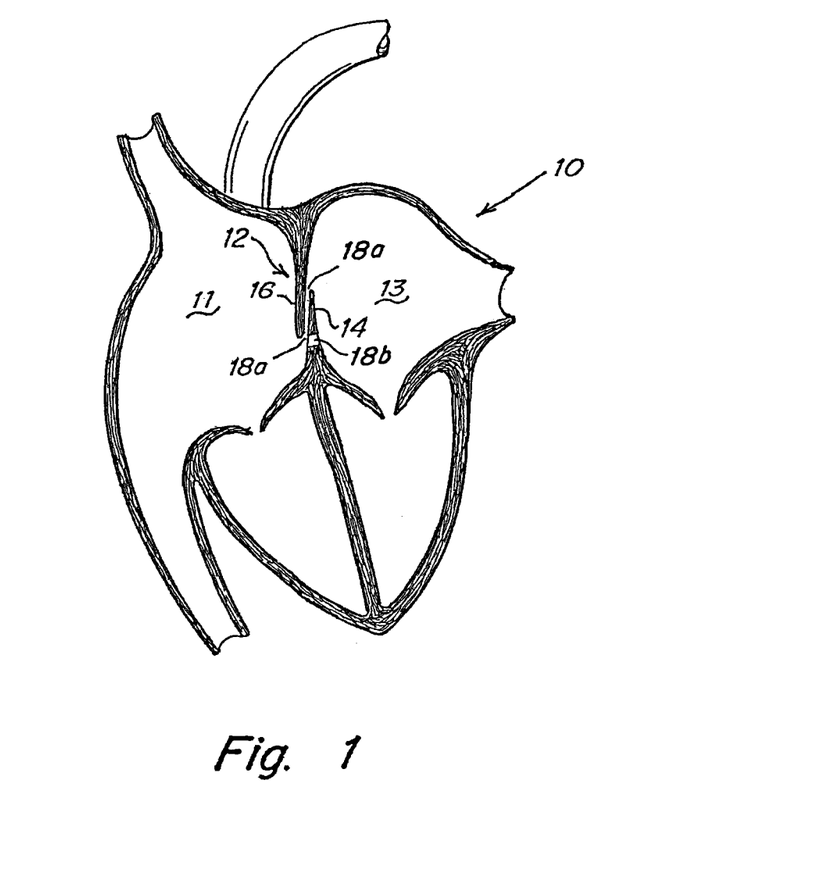
FIG. 1 is a schematic representation of a human heart including various septal defects.

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovale serves a desired purpose when a fetus is gestating. Because blood is oxygenated through the umbilical cord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. In addition, there is significant evidence that patients with a PFO who have had a cerebral vascular event are at increased risk for future, recurrent cerebrovascular events.

Accordingly, patients at such an increased risk are considered for prophylactic medical therapy to reduce the risk of a recurrent embolic event. These patients are commonly treated with oral anticoagulants, which potentially have adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close a PFO. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are significant complications due to thrombus, fractures of the components, conduction system disturbances, perforations of heart tissue, and residual leaks. Many devices have high septal profile and include large masses of foreign material, which may lead to unfavorable body adaptation of a device. Given that ASD devices are designed to occlude holes, many lack anatomic conformability to the flap-like anatomy of PFOs. Thus, when inserting an ASD device to close a PFO, the narrow opening and the thin flap may form impediments to proper deployment. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

The techniques disclosed herein are designed to address these and other deficiencies of prior art septal closure devices and techniques for delivering and retrieving such devices.

SUMMARY OF THE INVENTION

This specification discloses catch systems and techniques for catching an implant in its deployed configuration. These devices and techniques relate particularly to, but are not limited to, a septal occluder made from a polymer tube. These devices and techniques, in addition to use with septal occluders, could be applied to other medical devices, such as other expandable devices constructed from an underlying tubular structure.

A catch system is disclosed that reduces and maintains the reduced axial length of the device in its deployed configuration. Also, varied constructions could be used to maintain the axial dimension of the device. In some embodiments, a catch member secures the ends of the occluder in a compressed position. Preferably it secures both sides of the device in the deployed position with a single catch member. In one aspect, the catch member includes a ridge to provide a friction fit to catch the deployed occluder. In another aspect, the catch member includes a compressible tip. The tip can be compressed to reduce the profile of the compressible portion, especially to facilitate delivery and deployment. When the occluder is released from the delivery system and during the deployment process, the compressible tip expands such that the friction fit provided by the ridge, or other catch mechanism, is engaged. In another aspect, the catch member includes a temporary catching mechanism to temporarily secure the occluder in a compressed position before the catch mechanism is fully engaged. In one embodiment, a cylindrical portion of the catch member along which the occluder slides includes a first portion having a first diameter and a second portion having a second diameter. A portion of the occluder having an inner diameter smaller than the larger diameter removably catches on the larger diameter to temporarily secure the occluder in a compressed position before the catch mechanism is fully engaged.

These and other aspects and embodiments of the disclosure are illustrated and described below.

DETAILED DESCRIPTION OF THE INVENTION

The present disclosure provides devices, delivery/retrieval systems and techniques for delivering such devices intended to occlude an aperture within body tissue. In particular and as described in detail below, the described occluder may be used for closing an ASD or PFO in the atrial septum of a heart. Although the embodiments are described with reference to an ASD or PFO, one skilled in the art will recognize that the device and methods of the present invention may be used to treat other anatomical conditions. As such, the invention should not be considered limited in applicability to any particular anatomical condition. In addition, the systems and methods for delivery and retrieval, and for catching a device in a deployed state, which are aspects of the present invention may also be used in connection with other types of devices besides an occluder, in particular, devices having tubular profiles.

FIG. 1 illustrates a human heart 10, having a right atrium 11 and a left atrium 13 and including various anatomical apertures 18a and 18b. The atrial septum 12 includes septum primum 14 and septum secundum 16. The anatomy of the septum 12 varies widely within the population. In some people, septum primum 14 extends to and overlaps with septum secundum 16. The septum primum 14 may be quite thin. When the anatomical apertures 18a is present, blood could travel through the anatomical aperture 18a between septum primum 14 and septum secundum 16 (referred to as "the PFO tunnel"). Additionally or alternatively, the presence of an ASD could permit blood to travel through an aperture in the septal tissue, such as through the anatomical aperture 18b.

In this application, "distal" refers to the direction away from a catheter insertion location and "proximal" refers to the direction nearer the insertion location. Additionally, the term "delivery configuration" refers to the configuration of a device, such as an occluder, when it has a reduced profile in a delivery catheter. The term "deployed configuration" refers to the configuration of the device, such as an occluder, when it has deployed from the catheter, such as at the desired implantation location.

Figure 2:
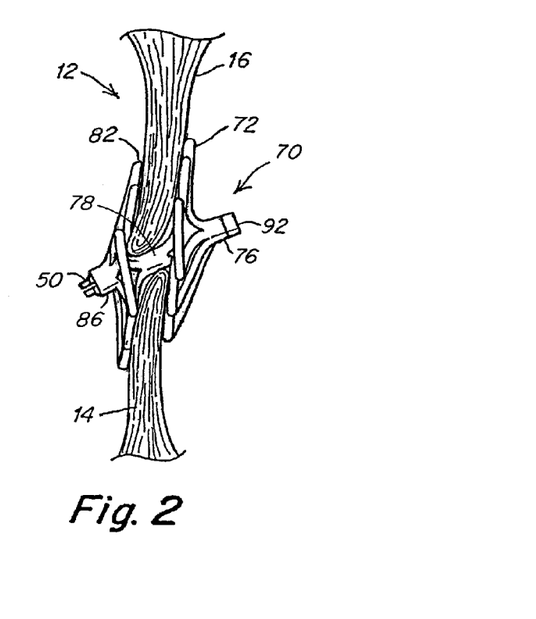
FIG. 2 illustrates a deployed occluder according to an aspect of the disclosure.

FIG. 2 illustrates an exemplary occluder with which systems and techniques disclosed herein may be used. An occluder 70, for example, is illustrated as deployed in the septum 12 of a heart. The device operates to close an aperture in the septum by securing the septum in a closed manner. The reference numerals used to identify components of the described embodiment are disposed on multiple figures where the component is illustrated. The reference numerals are intended to facilitate an overall understanding of the invention and the relationship between components illustrated in different figures.

The embodiment described in conjunction with FIGS. 5-8 has some similarities to the device disclosed in U.S. patent application Ser. No. 10/890,784, entitled Tubular Patent Foramen Ovale (PFO) Closure Device with Locking Mechanism, filed on Jul. 14, 2004; U.S. Patent Application No. 60/549,741, entitled Delivery/Recovery System for Clover Leaf Septal Occluder, filed on Mar. 3, 2004; U.S. Patent Application No. 60/612,857, entitled Delivery/Recovery Systems for PFO Occluder with Catch System, filed Sep. 24, 2004; U.S. Patent Application No. 60/663,289, filed Mar. 18, 2005, entitled Delivery/Recovery System for PFO Occluder with Catch System; U.S. Patent Application No. 60/662,990, filed Mar. 18, 2004, entitled Suture Delivery/Recovery System for PFO Occluder with Catch System; all of which have the same assignee as the present application, and are incorporated herein by reference in their entirety. These incorporated documents describe how a device can be formed by making cuts or slits in a tube and compressing the ends, and how to deliver such a device.

Figures 5, 6, 7:
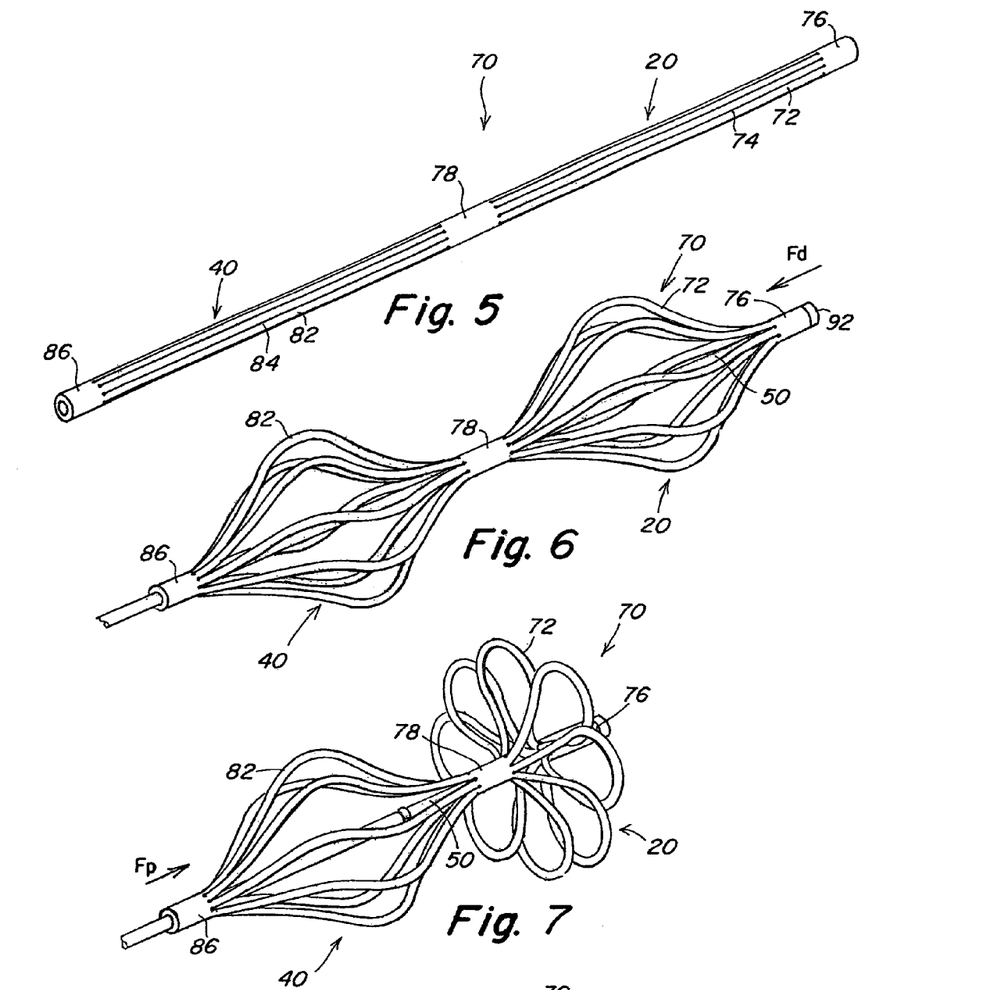
FIGS. 5-8 illustrate an occluder according to the present invention in a sequence between a reduced profile delivery configuration (FIG. 5) and an expanded profile deployed configuration (FIG. 8).
Figure 8:
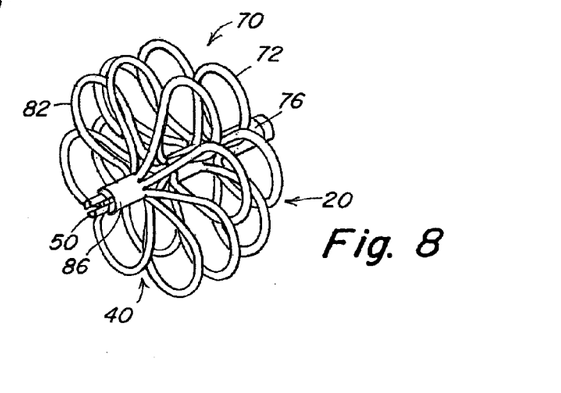

As shown in FIGS. 5-8, the occluder 70 is formed from a tube (which can be extruded or rolled) that forms distal petals 72 produced by slits 74 in the distal portion of tube according to the cutting pattern shown in FIG. 5. As shown in FIG. 6, the distal portion 20 of the tube includes 8 slits 74 that form 8 extended segments of the tube that form the distal loops or petals 72. As apparent from the figures, the slits extend the entire distance of the distal portion of the tube between central tube 78 and distal end 76 so that the loops of the same cross section are formed. Upon application of force $F_d$ to distal end 76, extended segments defined by slits 74 bow and twist outward to form distal petals 72 in distal side of the occluder 70. The movement of the segments during deployment is such that the segments rotate in an orthogonal plane relative to the axis of the device. Central tube 78 may be constrained during the application of force $F_d$, or any combination of forces sufficient to reduce the axial length of the tube may be applied. One end of each of distal petals 72 originates from central tube 78, while the other end originates from distal end 76 (FIGS. 6 and 7). Proximal petals 82 may be formed in proximal portion 40, as shown in FIGS. 6-8, making slits 84 between central tube 78 and proximal end 86 using the same cutting pattern described above, and applying force $F_p$ or combination of forces sufficient to reduce the axial length of the tube, allowing struts 82 to bow and twist outward to form proximal petals 82 in proximal portion 40 of the occluder 70. One end of each of distal petals 82 originates from central tube 78, while the other end originates from proximal end 86.

The tube(s) forming occluder 70 may be formed from a biocompatible metal or polymer. In at least some embodiments, the occluder 70 is formed of a bioabsorbable polymer, or a shape memory polymer. Shape memory polymers can be advantageous so that the structure of the device assists in pressing the PFO tunnel closed. In other embodiments, the occluder 70 is formed of a biocompatible metal, such as a shape memory alloy (e.g., nitinol). The thermal shape memory and/or superelastic properties of shape memory polymers and alloys permit the occluder 70 to resume and maintain its intended shape in vivo despite being distorted during the delivery process. Alternatively, or additionally, the occluder 70 may be formed of a bioabsorbable metal, such as iron, magnesium, or combinations of these and similar materials. Exemplary bioabsorbable polymers include polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated by reference in their entirety.

The cross-sectional shape of tube may be circular or polygonal, for example square, or hexagonal. The slits 74, 84 may be disposed on the face of the polygon (i.e., the flat part) or on the intersection of the faces.

The tube can be injection molded, extruded, or constructed of a sheet of material and rolled into a tube. The sheet of material could be a single ply sheet or multiple ply. The slits that form the segments could be cut or stamped into the sheet prior to rolling the sheet into a tube to connect the ends to form an enclosed cross section. Various geometrical cross sections are possible including circular, square, hexagonal and octagonal and the joint could be at the vertex or along the flat of a wall if the cross section is of a particular geometry. Various attachment techniques could be used to join the ends of the sheet to form a tube, including welding, heat adhesives, non-heat adhesives and other joining techniques suitable for in-vivo application.

The petal configuration, illustrated in FIG. 8, is the deployed configuration. The occluder 70 can be secured in the petal configuration by a catch system that holds the ends of the tube together, certain embodiments of which are described below.

The transformable design of occluder 70 enables occluder 70 to be delivered in a low-profile, delivery configuration, and to be converted readily, i.e., by reducing the axial length, in place to the high-profile, deployed configuration. Moreover, the conversion can readily be effected by forcing distal end 76 and proximal end 86 closer together. For example, distal portion 20 and proximal portion 40 of occluder 70 may be deployed in separate steps, or both distal portion 20 and proximal portion 40 of occluder 70 may be exposed (e.g., out of the delivery catheter) prior to engaging the catch system and deployed together as the catch member is engaged. Use of the terms distal and proximal portions 20 and 40, respectively, include the loops or other geometries and configurations that are formed on the distal and proximal sides, respectively.

Occluder 70 may be made in any one of several ways. Slits 74 and 84 may be cut such that tube bends into its intended configuration following deployment in vivo. Specifically, slits 74 and 84 may be cut to produce segments 72 and 82 (as illustrated in FIGS. 5, 6) of a thickness that facilitates the bending and formation of loops 72 and 82 (as illustrated in FIGS. 7, 8) upon the application of forces $F_d$ and/or $F_p$ during deployment. The segments 72 and 82 that form the loops are referenced with the same reference numeral. As an alternative, or additionally, a tube formed of a shape memory material may be preformed into its intended configuration ex vivo so that it will recover its preformed shape once deployed in vivo. According to at least some embodiments, this preforming technique produces more reliable deployment and bending of occluder 70 in vivo. An intermediate approach may also be used: tube may be only slightly preformed ex vivo such that it is predisposed to bend into its intended shape in vivo upon application of forces $F_d$ and/or $F_p$.

FIG. 2 shows a deployed occluder 70 in a human heart with a catch member 50 engaged (much of the catch member is obscured by the central tube of the occluder). The term "catch system" describes the portion/aspect of the device that secures the device in the deployed configuration, it may be a single piece or a group of connected or assembled pieces. The catch member is the portion of the catch system that engages with the occluder to hold the occluder in the deployed configuration and is described in more detail below.

This particular type of occluder 70 and delivery sequences are described for purposes of illustration and explanation; of course, other types of occluders can be deployed using the deployment catch systems described herein. The catch member 50, as illustrated, is disposed in an radially central location in the occluder 70 and is schematically illustrated as a separate piece than the occluder 70. In a preferred embodiment, the catch member may be fixed to one end of the tube that forms occluder 70. For example, a flange 92 may be fixed to the distal end 39 (shown in FIG. 6 and FIG. 10) of the tube.

In general, references to "occluder 70" herein may be inclusive of catch member 50, depending on the context, for example, unless separately listed or otherwise stated. One end of tube, preferably proximal end 86, is able to move with respect to the catch member 50 (and especially the catch system) so that the distal and proximal petals 72 and 82 can move from the delivery configuration to the deployed configuration. The inside surface of the tube is able to slide over the catch member 50 so that, when the proximal end of the occluder 70 rests against a proximal ridge of catch member 50, the occluder 70 is secured in its deployed configuration. The catch member 50 is included in the catch system that includes a portion for connection to the delivery/recovery system, including, for example, a threaded section illustrated and described in more detail below.

Figure 3:
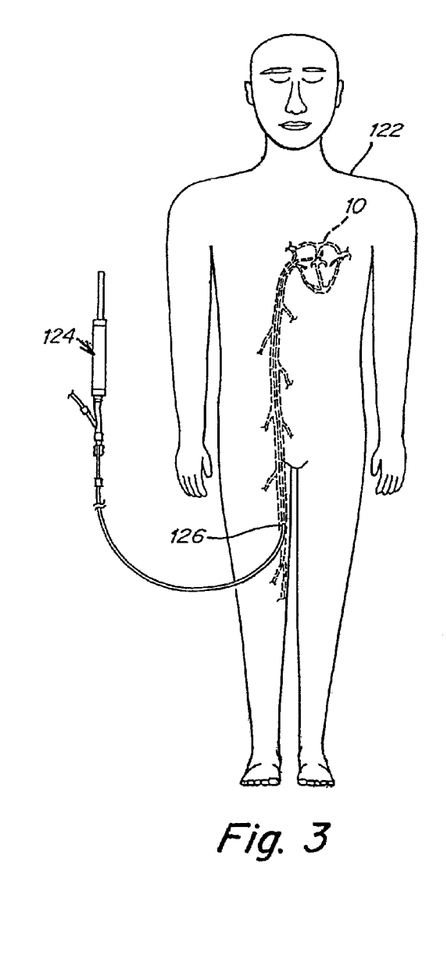
FIG. 3 illustrates introduction of the occluder in a human heart using a delivery system in accordance with an aspect of the disclosure.
Figure 4:
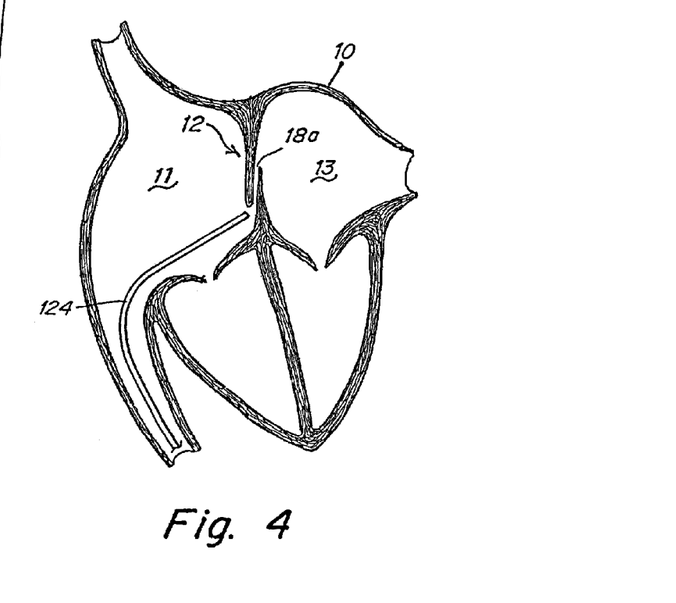
FIG. 4 illustrates a detail view of a delivery catheter in a heart with its tip approaching a patent foramen ovale between the left atrium and right atrium.

FIG. 3 illustrates the insertion of an occluder 70 in a human subject 122 using a delivery assembly 124 in accordance with an aspect of the disclosure. A portion of delivery assembly 124, including an occluder 70 and a delivery mechanism for the occluder 70, which can be externally manipulated by a clinician, is inserted into the subject through an incision point 126. The distal end of the delivery assembly is advanced toward and into the heart 10 until the distal end is in proximity to the defect to be closed, as seen in FIG. 4.

Figure 9A:
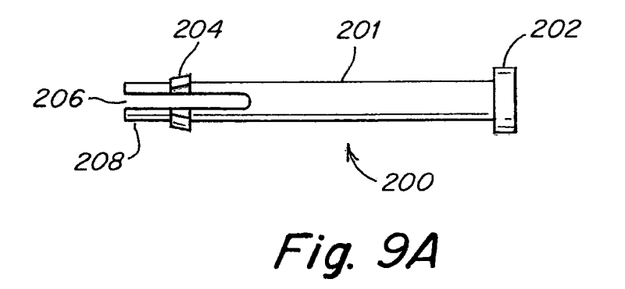
FIG. 9A is a side view of a catch member with a compressible tip in accordance with one aspect of the disclosure.

FIG. 9A shows an embodiment 200 for a catch member, that includes a collapsible tip. The catch member 200 includes a cylindrical catch body 201 and a distal flange 202 (which is the same as flange 92 in FIGS. 2 and 6). The catch member 200 includes a proximal ridge 204 disposed on its proximal portion and a slot 206 at its proximal end. The catch member 200 also includes a proximal tip 208, which can be adapted for connection to a portion of the delivery system. For example, it may be threaded. The distal flange 202 of the catch member 200 engages the distal end 39 of the occluder 70. The proximal ridge 204 of the catch member 200 engages the proximal end 44 of the occluder 70, holding the occluder 70 in its deployed configuration. The proximal tip 208 of the catch member 200 is collapsible; that is, due to slot 206, the diameter of the proximal portion of the catch member 200 can be reduced by compressing the sides of the proximal tip 208. The collapsible proximal tip 208 of the catch member 200 facilitates delivery and deployment of the occluder 70.

Figure 9B:
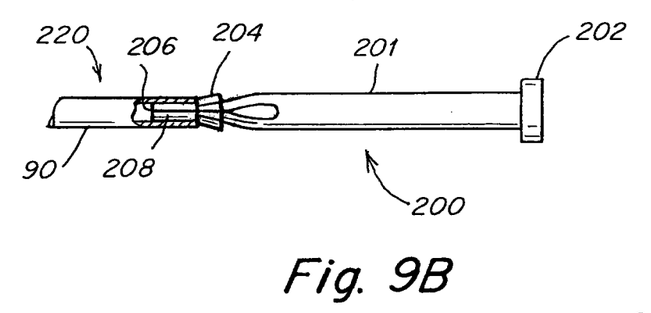
FIG. 9B is a side view of a catch member with a compressible tip in accordance with one aspect of the disclosure, in a delivery configuration.

A portion 220 of a delivery assembly 124 is shown in FIG. 9B. During delivery, the collapsible proximal tip 208 of the catch member 200 can be fixed in the compressed configuration by an inner catheter 90 due to the flexibility introduced by the slot 206, for example. This reduced profile enables the proximal ridge 204 of the catch member 200 to slide more easily through the central tube 78 and proximal end 86 of the occluder 70. This means that reduced force typically will be sufficient to force the occluder 70 into the deployed configuration and the device is less likely to be damaged by the deployment process. When the inner catheter 90 is removed, slot 206 is opened and the proximal tip 208 expands back into its original configuration shown in FIG. 9A. When slot 206 is opened and the proximal tip 208 of the catch member is in its original configuration, the diameter of the proximal ridge 204 is greater than the diameter of the catch body 201.

Figure 9C:
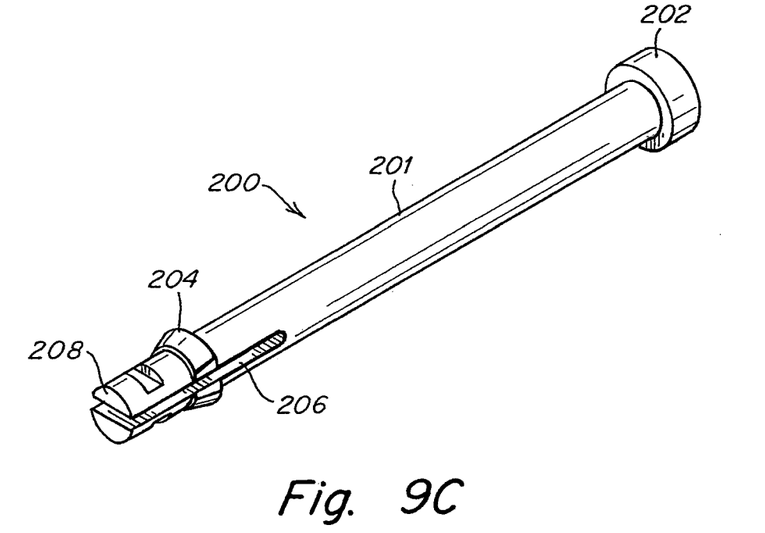
FIG. 9C is a perspective view of a catch member with a compressible tip in accordance with one aspect of the disclosure.

FIG. 9C is a perspective view of the catch member 200. In an exemplary embodiment of catch member 200, catch body 201 has a length of about 0.6 inch and a diameter of about 0.065 inch. The proximal ridge 204 has a length of about 0.04 inch and a diameter of about 0.075 inch. The proximal tip 208 has a length of about 0.05 inches past the proximal ridge 204 and a diameter of about 0.070 inch, slightly larger than the diameter of the catch body 201. It is understood that the diameter of the proximal tip 208 can also be the same as the diameter of the catch body 201. The slot 206 has a length of about 0.25 inches and a width of about 0.020 inches. The distal flange 202 has a diameter of about 0.08 inch. In another embodiment of the catch member 200, the catch body 201 has a length of about 1.2 inch and a diameter of about 0.058 inch. The proximal ridge 204 portion has a length of about 0.02 inch and a normal diameter of about 0.08 inch. The proximal tip 208 has a length of about 0.18 inch past the proximal ridge 204 and a normal diameter of about 0.070 inch, slightly larger than the diameter of the catch body 201. The slot 206 has a length of about 0.300 inches and a width of about 0.020 inch. These dimensions are approximate and provided by way of example only.

In certain embodiments, it is desirable for the catch body 201 of the catch member 200 to have some interference with the inner portion of the occluder 70 as the occluder 70 slides over the catch member 200 into the deployed configuration. The interference is provided by dimensioning the catch body 201 so that the catch body 201 has a diameter close to an inner diameter of the occluder 70, particularly an inner diameter of the proximal portion of the occluder 70, even while the proximal tip 208 of the catch member 200 is in its compressed position. This friction will provide a temporary catch mechanism, which will tend to "stick" the occluder 70 in a partially deployed configuration before the catch member 200 is fully activated.

Figure 10A:
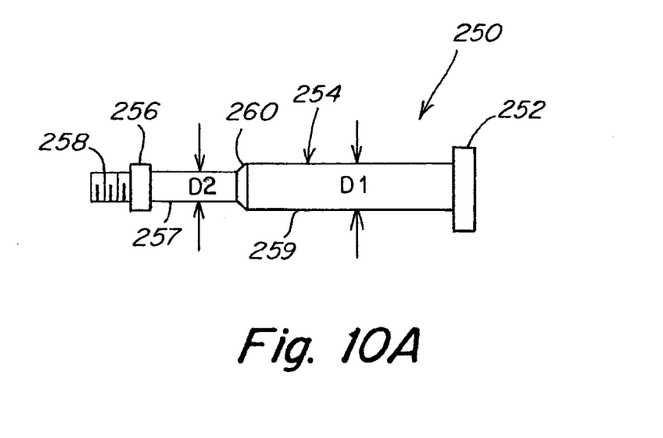
FIG. 10A is a side view of a catch member in accordance with one aspect of the disclosure.
Figure 10B:
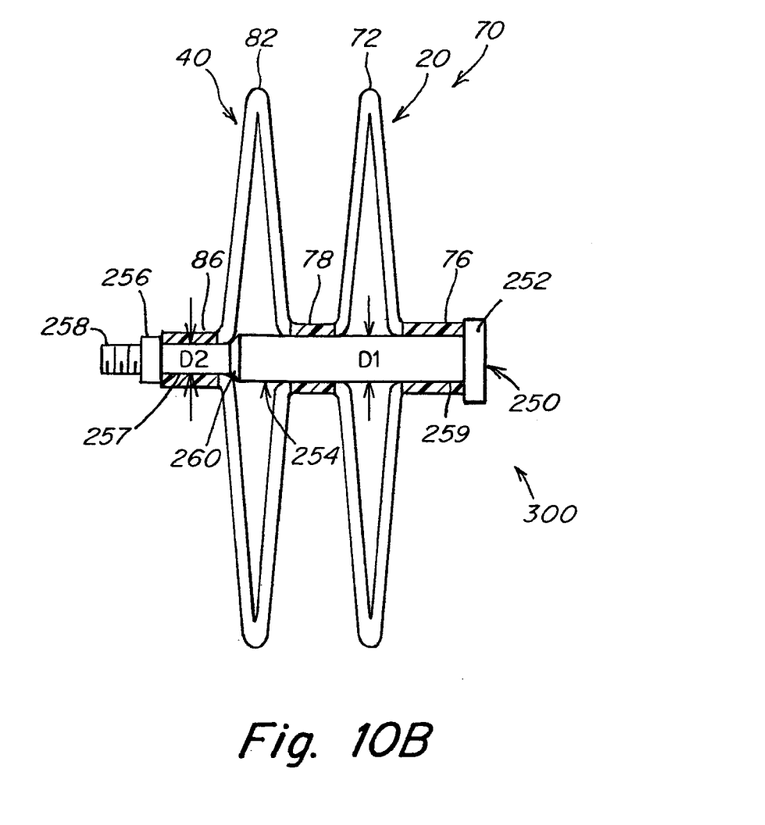
FIG. 10B is a side view of a catch member and an occluder in accordance with one aspect of the disclosure.

FIG. 10A illustrates another embodiment of a catch member 250. This catch member 250 also provides a "temporary" catch for the device that holds the occluder 70 in its partially deployed configuration during the deployment process before the catching mechanism is completely secured. Catch member 250 includes a distal flange 252, a catch body 254, a proximal tip 258, and a proximal ridge 256. The relative diameter of the proximal ridge 256 to the proximal tip 258 may be smaller than illustrated in FIG. 10A. The basic function of catch member 250 is similar to the function of catch member 50 and catch member 200. As shown in FIG. 10B, which illustrates an occluder assembly 300 including an occluder 70 and catch member 250, when the occluder 70 is deployed, the catch member 250 maintains the occluder 70 in a reduced axial length position, its deployed configuration. FIG. 10 is a schematic illustration and shows the proximal ridge 256 having an exaggerated diameter. The distal flange 252 and proximal ridge 256 of the catch member 250 provide interference fits with respective ends of the occluder 70 and keep the occluder 70 in its deployed configuration. The catch body 254 of this catch member 250 has a tapered or graduated cylindrical profile, composed of two sections having two different diameters. A distal section 259 has a first diameter $D_1$ and a proximal section 257 has a second diameter $D_2$. The distal section 259 and the proximal section 257 are joined by a sloped section 260.

In certain embodiments, the first diameter $D_1$ of the distal section 259 of the catch body 254 is greater than the second diameter $D_2$ of the proximal section 257 of the catch body 254. The sloped section 260 can have a shallow or a steep slope. The occluder 70 is formed of a tubular element that defines one or more inner diameters. In certain embodiments, the difference in the first and second diameters $D_1$ and $D_2$ corresponds to a similar difference in the inner diameters of respective portions of the occluder 70. For example, in some embodiments, the distal end 76, distal portion 20 of the occluder 70 have an inner diameter that is similar to the first diameter $D_1$ of the distal section 259 of the catch body 254. The central tube 78, proximal portion 40 and proximal end 86 of the occluder 70 have an inner diameter similar to the second diameter $D_2$ of the proximal section 257 of the catch body 254. During deployment, the distal portion 20 and central tube 78 of the occluder 70 ride over the catch body 254. Due to similarity in diameter dimensions, the interference between the distal portion 20, central tube 78 of the occluder 70 and the distal section 259 of the catch body 254 allows the distal portion 20 of the occluder 70 being temporarily caught at the partial deployed configuration, and therefore provide operator with full control of the deployment process. The proximal portion 40 can only travel over the proximal section 257 of the catch member 250 until the proximal portion 40 reaches the sloped section 260 of the catch body 254 and is blocked by the gradient between the first diameter $D_1$ and the second diameter $D_2$. The proximal portion 40 of the occluder 70 then gets wedged behind the proximal ridge 256 of the catch member 250 and thereby catches the occluder 70 in its deployed configuration. Similarly, the interference between the proximal portion 40 of the occluder 70 and the proximal section 257 of the catch member 250 allows the proximal portion 40 of the occluder 70 to be temporarily caught at partial deployed configuration. According to an alternative embodiment, the distal portion 20 and central tube 78 of the occluder 70 ride smoothly over the distal section of the catch body 254, while the proximal section 40 of the occluder 70 interferes with the proximal section 257 of the catch member 250, thereby providing a partial catch.

According to an alternative embodiment, the inner diameter of the entire length of the occluder 70 is similar to the second diameter of the distal section 259 of the catch body 254. The distal portion 20, central tube 78, and proximal portion 40 of the occluder 70 ride over the catch body 254.

Similarly, the interference distal portion 20, central tube 78, proximal portion 40 of the occluder 70 and the distal section 259 of the catch body allows the occluder 70 being temporarily caught during the deployment process. In preferred embodiments, this feature is combined with the compressible proximal tip 258 described above. By this mechanism, the occluder 70 can be held in place while the compressible proximal tip 258 is still secured to the delivery system and before it is expanded into its final deployment position.

Figure 10C:
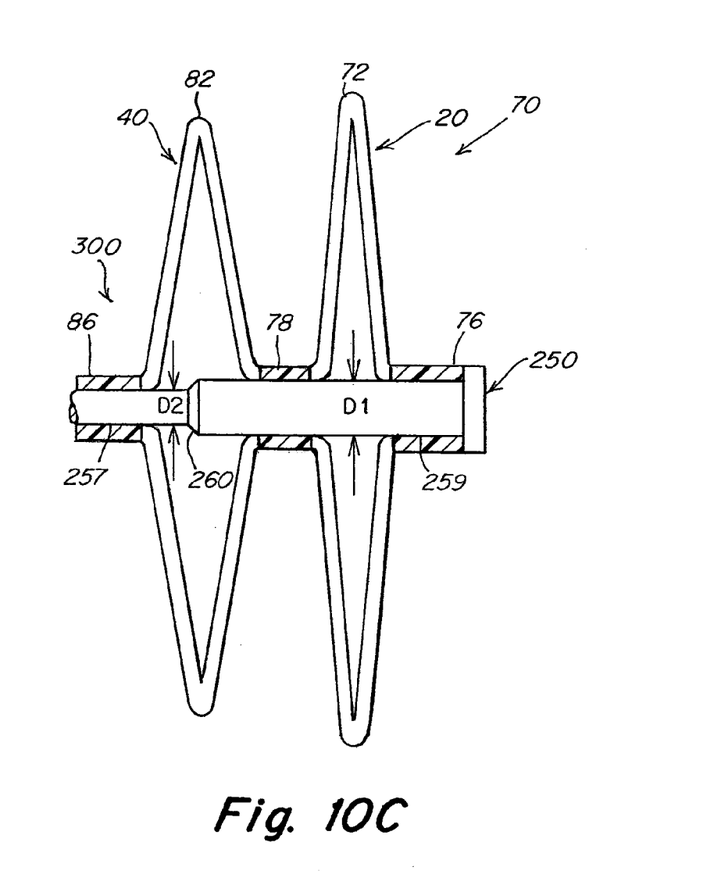
FIG. 10C is a close-up view of a portion of a catch member and an occluder in accordance with one aspect of the disclosure.
Figure 10D:
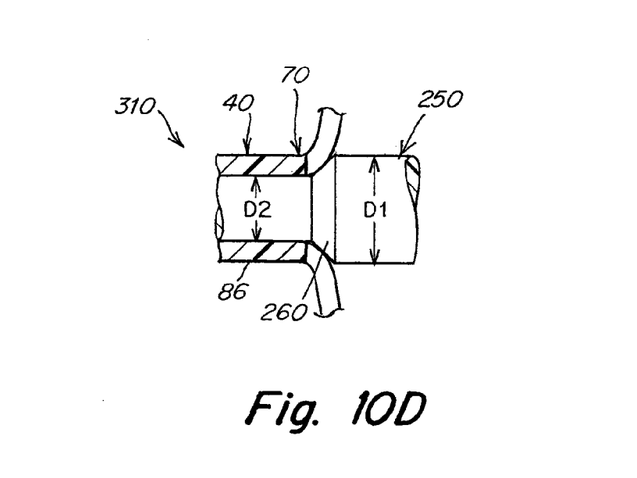
FIG. 10D is a close-up view of a portion of a catch member and an occluder in accordance with one aspect of the disclosure.

FIGS. 10C and 10D provide more detailed cross-sectional views of portions 300 and 310 of the occluder 70 and catch member assembly 300, and of the interaction between the inner portion of the occluder 70 and the catch member 250.

The embodiment illustrated in FIGS. 10A-10C is particularly useful to provide a temporary catch mechanism that enables the occluder to remain in a partially deployed configuration when the occluder is held in a fixed position with respect to the catch member by the interference fit between the catch member and the occluder.

The embodiments and techniques described here are described preferably for use with a device made of a polymer and formed from a single tube, such that the tube is a single monolithic material. The catch mechanism can be all or partly monolithic or integral with the tubular structure, or there can be an absence of any type of bonding or rigid connection to the rest of the tubular structure, in which case there may be some spring force or other force that holds the catch mechanism in place. While the device is thus shown as being substantially formed from a single tubular body, the catch mechanism as described in the embodiments above could be used with other types of devices, including those formed from many pieces, and including devices formed from other materials, including stainless steel or Nitinol.

In cases in which the device is made of a polymer, it can be desirable to add an additive or coating to the material to make it radiopaque to make it more visible in a wider variety of imaging techniques.

While a compressible tip for a catch member has been described has having a single slot, it will be appreciated that a compressible tip could be implemented using other techniques, for example, by providing multiple slots.

It will be appreciated that while a particular sequence of steps has been shown and described for purposes of explanation, the sequence may be varied in certain respects, while still obtaining the desired deployment or in some cases to effect deployment in a particular way. For example, the delivery sheath may be advanced or retracted at varying times and in varying degrees, the proximal and distal portions of the occluder may be deployed into the looped configuration in a different sequence, etc.

Having described many embodiments, it should be apparent that modifications can be made without departing from the scope of the present invention.

What is claimed is:

1. A collapsible medical device for occluding an aperture in a body, the medical device having a first configuration as a reduced profile and a second configuration as an expanded profile, the medical device being adapted to be delivered through a delivery system into a desired delivery location, the medical device comprising:
    a bioresorbable occluder portion movable between the first and the second configuration, wherein the occluder portion comprises a proximal end, a distal end, and an axial passage between the proximal end and the distal end, the axial passage having a first inner diameter at the proximal end and a second inner diameter at the distal end;
    a catch member adapted to be disposed in the axial passage of the occluder portion, wherein the catch member comprises a catch body having a proximal portion and a distal flange,
    wherein the distal flange of the catch member engages the distal end of the occluder portion,
    wherein the catch body has a tapered or graduated cylindrical profile composed of a distal section having a first diameter $D_1$ and a proximal section having a second diameter $D_2$ joined by a sloped section, wherein diameter $D_2$ is similar to the first inner diameter of the axial passage of the occluder portion; and,
    wherein the proximal portion of the catch body of the catch member further comprises two compressible prongs each comprising a proximal tip and a proximal ridge on a surface of the prong, wherein the proximal tip is adapted for connection to a delivery system; and the proximal ridge is adapted to pass through the axial passage of the occluder portion while the compressible prongs are held in a compressed position and to engage the proximal end of the occluder portion thereby holding the medical device in the second configuration.

2. The collapsible medical device of claim 1, wherein the occluder portion is a bioresorbable polymer.

3. The collapsible medical device of claim 2, wherein the bioresorbable polymer is poly-4-hydroxy-butyrate (P4HB).

4. The collapsible medical device of claim 1, wherein the occluder portion is a bioresorbable metal.

5. The collapsible medical device of claim 1, wherein further the proximal collapsible tip is threaded.

6. A collapsible medical device for occluding an aperture in a body, the medical device having a first configuration as a reduced profile and a second configuration as an expanded profile, the medical device being adapted to be delivered through a delivery system into a desired delivery location, the medical device comprising:
    a bioresorbable occluder portion movable between the first and the second configuration, wherein the occluder portion comprises a proximal end and proximal portion having a proximal axial passage therethrough with an inner diameter, a distal end and a distal portion having a distal axial passage therethrough with an inner diameter, and a central tube between the proximal end and the distal end; and
    a catch member adapted to be disposed in the axial passages of the occluder portion, wherein the catch member comprises a catch body having an outer surface; a proximal section comprising a proximal collapsible tip, a proximal ridge adjacent the proximal collapsible tip and a slot disposed at the proximal collapsible tip to render it collapsible; and a distal section comprising a distal flange;
    wherein the distal flange of the catch member engages the distal end of the occluder portion,
    wherein the catch body has a tapered or graduated cylindrical profile composed of the distal section having a first outer diameter $D_1$ and the proximal section having a second outer diameter $D_2$ joined by a sloped section, wherein diameter $D_2$ is similar to the inner diameter of the proximal axial passage of the occluder portion; and,
    wherein the proximal collapsible tip is adapted for connection to a delivery system; and the proximal ridge is adapted to pass through the proximal axial passage of the occluder portion while the proximal collapsible tip is held in a collapsed position to enable delivery and deployment of the occluder.

7. The collapsible medical device of claim 6, wherein the occluder portion is a bioresorbable polymer.

8. The collapsible medical device of claim 7, wherein the bioresorbable polymer is poly-4-hydroxy-butyrate (P4HB).

9. The collapsible medical device of claim 6, wherein the occluder portion is a bioresorbable metal.

10. The collapsible medical device of claim 6, wherein further the proximal collapsible tip is threaded.

* * * * *